(12) United States Patent
Shen et al.

(10) Patent No.: US 9,157,843 B2
(45) Date of Patent: Oct. 13, 2015

(54) TESTING METHOD OF BENDING STRESS AND TESTING APPARATUS THEREOF

(71) Applicant: Industrial Technology Research Institute, Hsinchu (TW)

(72) Inventors: Chih-Ming Shen, New Taipei (TW); Guo-Shing Huang, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 78 days.

(21) Appl. No.: 13/861,390

(22) Filed: Apr. 12, 2013

(65) Prior Publication Data

US 2014/0174195 A1    Jun. 26, 2014

(30) Foreign Application Priority Data

Dec. 21, 2012  (TW) .............................. 101149169 A (51) Int. Cl.
*G01N 3/20* (2006.01)

(52) U.S. Cl.
CPC .......... *G01N 3/20* (2013.01); *G01N 2203/0282* (2013.01); *G01N 2203/0435* (2013.01)

(58) Field of Classification Search
CPC ..................................................... G01N 3/20
See application file for complete search history.

(56) References Cited

U.S. PATENT DOCUMENTS

| | | | |
|---|---|---|---|
| 3,934,773 A | 1/1976 | Chinnock et al. | |
| 4,711,654 A | 12/1987 | Iida | |
| 5,594,178 A | 1/1997 | Takahashi et al. | |
| 5,992,242 A | 11/1999 | Murphy et al. | |
| 6,016,377 A | 1/2000 | Suhir | |
| 6,119,527 A | 9/2000 | Suhir | |
| 6,776,050 B2 | 8/2004 | Auch et al. | |
| 7,461,564 B2 | 12/2008 | Glaesemann | |
| 2008/0216585 A1* | 9/2008 | Cipra | 73/851 |
| 2011/0092946 A1 | 4/2011 | Kline et al. | |

FOREIGN PATENT DOCUMENTS

| | | |
|---|---|---|
| CN | 102221503 | 10/2011 |
| CN | 102778390 | 11/2012 |

(Continued)

OTHER PUBLICATIONS

Matthewson et al., "Strength Measurement of Optical Fibers by Bending", Journal of the American Ceramic Society, Nov. 1986, vol. 69, p. 815-821.

(Continued)

*Primary Examiner* — Lisa Caputo
*Assistant Examiner* — Brandi N Hopkins
(74) *Attorney, Agent, or Firm* — Jianq Chyun IP Office (57) ABSTRACT

A testing method of bending stress and a testing apparatus thereof are provided. The method includes the following steps. A stress distribution model of a structure to be tested is built. Next, a testing sample of the structure to be tested is provided, and a force is applied on two ends of the testing sample to bend the testing sample till it breaks at a breaking point, so as to obtain a first distance between the two ends of the testing sample when the testing sample breaks, or a second distance from the breaking point to a closer end of the two ends. Next, a maximum principle stress value of the stress distribution model or a break point principle stress value at the breaking point of the stress distribution model is obtained according to the first distance or the second distance.

10 Claims, 5 Drawing Sheets

(56) References Cited

FOREIGN PATENT DOCUMENTS

| JP | 2004101228 | 4/2004 |
|----|------------|--------|
| TW | 200916748 | 4/2009 |
| TW | I358537 | 2/2012 |

OTHER PUBLICATIONS

Gulati et al., "62.1: Mechanical Reliability of LCD Panels under Static Loading", SID Symposium Digest of Technical Papers, May 2004, vol. 35, p. 1593-p. 1595.

Helfinstine et al., "62.2: Mechanical Reliability of LCD Panels under Dynamic Loading", SID Symposium Digest of Technical Papers, May 2004, vol. 35, p. 1597-p. 1599.

Gulati et al., "44.3: Mechanical Robustness of Thin AMLCD Glass Substrates Under Point Loading", SID Symposium Digest of Technical Papers, Jun. 2001, vol. 32, p. 1156-p. 1159.

Gulati et al., "45.2: Two Point Bending of Thin Glass Substrate", SID Symposium Digest of Technical Papers, Jun. 2011, vol. 42, p. 652-p. 654.

"Office Action of Taiwan Counterpart Application", issued on Aug. 27, 2014, p. 1-p. 4.

* cited by examiner

TESTING METHOD OF BENDING STRESS AND TESTING APPARATUS THEREOF

CROSS-REFERENCE TO RELATED APPLICATION

This application claims the priority benefit of Taiwan application serial no. 101149169, filed on Dec. 21, 2012. The entirety of the above-mentioned patent application is hereby incorporated by reference herein and made a part of this specification.

BACKGROUND

1. Technical Field

The disclosure relates to a testing method and a testing apparatus. Particularly, the disclosure relates to a testing method of bending stress and a testing apparatus thereof.

2. Related Art

In recent years, along with quick development of electronic technology, and emerging of high-tech electronics industries, more user-friendly and more powerful electronic products are quickly developed and have design features of lightness, slimness, shortness and smallness. In a convention technique, substrate thinning is a method of decreasing a weight and thickness of an electronic device. However, a bending strength of the thinned substrate is decreased, and a structure strength of the substrate is accordingly decreased.

Moreover, in the conventional technique, a required size of the substrate is formed through cutting. However, the substrate generally includes a fragile material such as glass, silicon substrate and ceramics, etc., and when the substrate is cut, a fracture surface is liable to have defects. If a cutting fracture surface of the substrate has small defects such as scars, cracks or foreign body, etc., when the substrate is bended, a problem of stress concentration is occurred around the defect, which may cause damage of the substrate. Therefore, quantitative measurement is required to obtain a bending stress strength of the substrate having a cutting defect, so as to determine whether the substrate is safe during a manufacturing process thereof or whether a structure of a finished product thereof is safe.

SUMMARY

The disclosure is directed to a testing method of bending stress, by which a bending stress of a material is tested through a simple, fast and effective manner, so as to obtain an accurate testing result.

The disclosure is directed to a testing apparatus of bending stress, which is adapted to implement the aforementioned testing method.

The disclosure provides a testing method of bending stress, which includes following steps. First, a stress distribution model of a structure to be tested is built. Then, a testing sample of the structure to be tested is provided, and a force is applied on two ends of the testing sample to bend the testing sample till it breaks at a breaking point, so as to obtain a first distance between the two ends of the testing sample when the testing sample breaks, and a second distance from the breaking point to a closer end of the two ends. Next, a maximum principle stress value of the stress distribution model or a breaking point principle stress value of the stress distribution model at the breaking point when the testing sample breaks is obtained according to the first distance or the second distance.

The disclosure provides a testing apparatus of bending stress, which is adapted to perform a bending stress testing on a testing sample. The testing apparatus includes two fixtures and a transmission unit. The two fixtures are disposed opposite to each other, and are adapted to move relative to each other along an axial direction. The two fixtures respectively have a carrying portion for leaning against the two ends of the testing sample, so as to apply the force on the two ends of the testing sample. The transmission unit is coupled to the two fixtures, and drives the two fixtures to move relative to each other along the axial direction to bend the testing sample.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1:
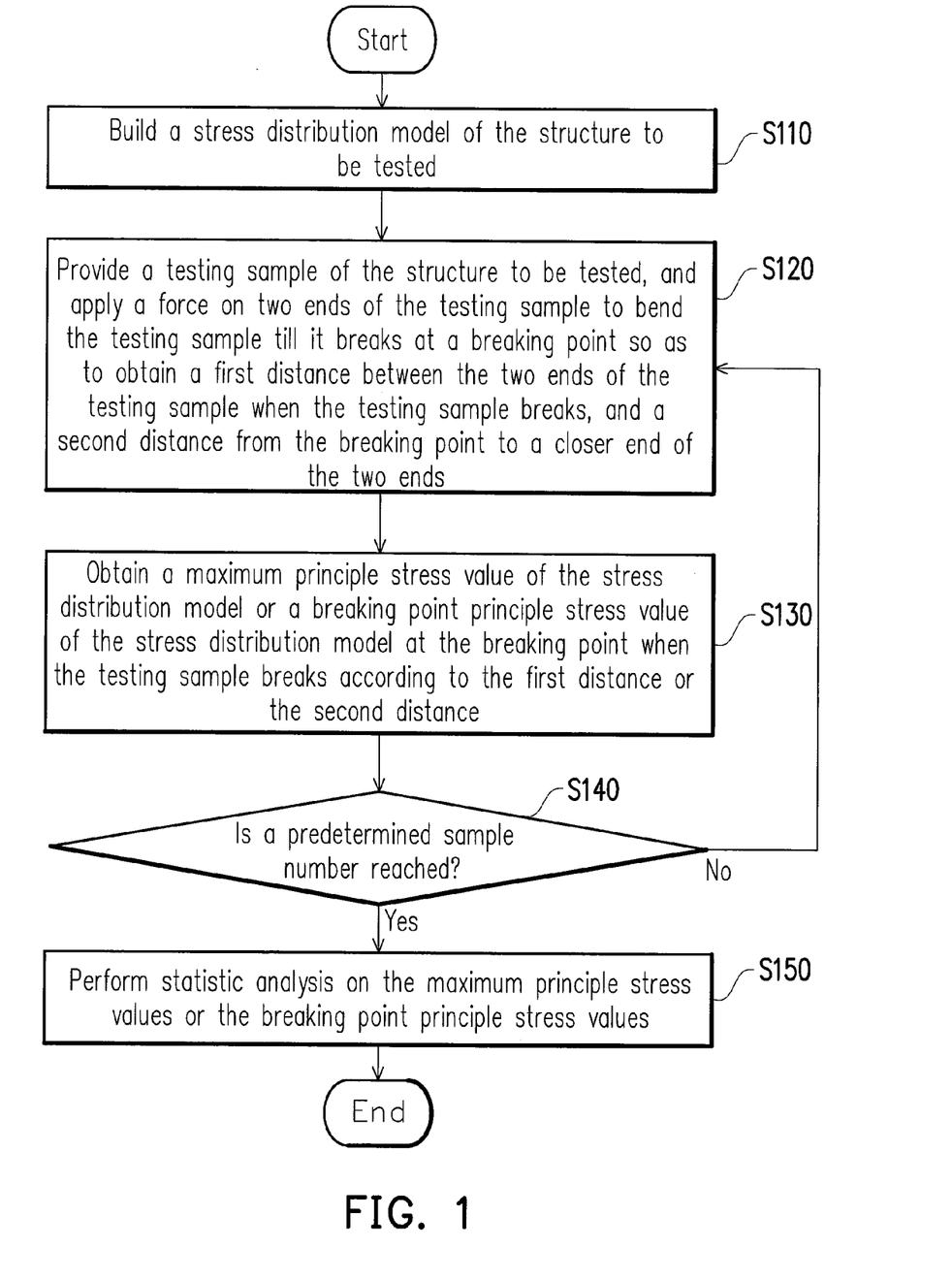
FIG. 1 is a flowchart of a testing method of bending stress according to an embodiment of the disclosure.
Figure 2:
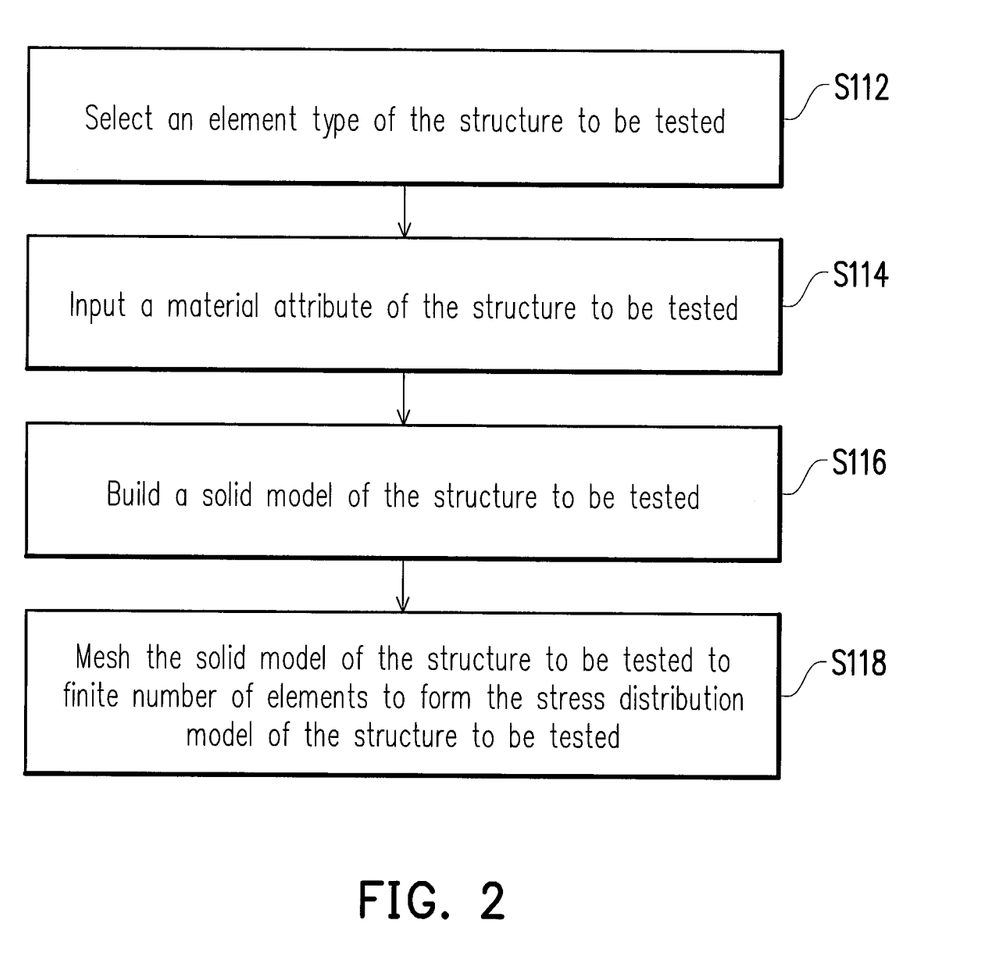
FIG. 2 is a flowchart of finite element analysis according to an embodiment of the disclosure.

FIG. 1 is a flowchart of a testing method of bending stress according to an embodiment of the disclosure. FIG. 2 is a flowchart of finite element analysis according to an embodiment of the disclosure. Referring to FIG. 1, the testing method of bending stress of the present embodiment is adapted to test a structure to be tested, and a material of the structure to be tested is for example, a fragile material. The testing method of bending stress includes following steps. First, in step S110, a stress distribution model of the structure to be tested is built. In the present embodiment, a method of building the stress distribution model includes finite element analysis (FEA). In detail, steps of the FEA are shown in the flowchart of FIG. 2, first, in step S112, an element type of the structure to be tested is selected. In the present embodiment, the element type of the structure to be tested is set to three-dimensional (3D) solid, shell or 2D element. Then, in step S114, a material attribute of the structure to be tested is input, where the material attribute of the structure to be tested includes Young's modulus and poisson's ratio of the structure to be tested, etc. Then, in step S116, a solid model of the structure to be tested is built. In step S118, the solid model of the structure to be tested is meshed to finite number of elements to form the stress distribution model of the structure to be tested. In this way, the stress distribution model of the structure to be tested that is established through the FEA is substantially completed.

Figure 3:
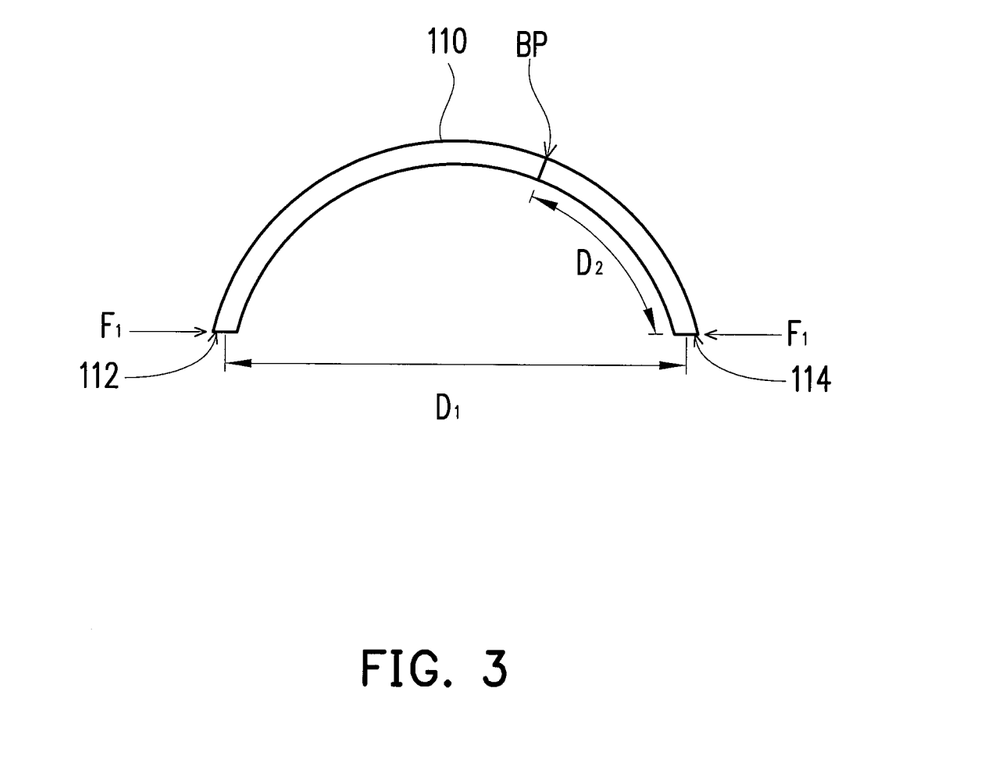
FIG. 3 is a schematic diagram of applying a force on two ends of a testing sample according to an embodiment of the disclosure.

FIG. 3 is a schematic diagram of applying a force on two ends of a testing sample according to an embodiment of the disclosure. Referring to FIG. 1 and FIG. 3, in step S120, a testing sample 110 of the structure to be tested is provided, and a force is applied on two ends 112 and 114 of the testing sample 110 to bend the testing sample 110 till it breaks at a breaking point BP, so as to obtain a first distance D1 between the two ends 112 and 114 of the testing sample 110 when the testing sample 110 breaks, and a second distance D2 from the breaking point BP to a closer end (which is the end 114 in FIG. 3) of the two ends 112 and 114. In the present embodiment, the structure to be tested is, for example, a glass substrate. In detail, the method of applying the force on the two ends 112 and 114 of the testing sample 110 to bend the testing sample 110 is to, for example, respectively apply horizontal forces F1 opposite to each other on the two ends 112 and 114 of the testing sample 110 to make the two ends 112 and 114 to approach to each other. A relative moving rate of the two ends 112 and 114 of the testing sample 110 can be controlled to be smaller than 10 mm/min, i.e. a stable force is provided to the two ends 112 and 114 of the testing sample 110, and relative movement between the two ends 112 and 114 of the testing sample 110 is slowly taken place, so as to achieve a quasi-static testing condition. In the present embodiment, the relative moving rate of the two ends 112 and 114 of the testing sample 110 is smaller than or equal to 1 mm/min.

Figure 4:
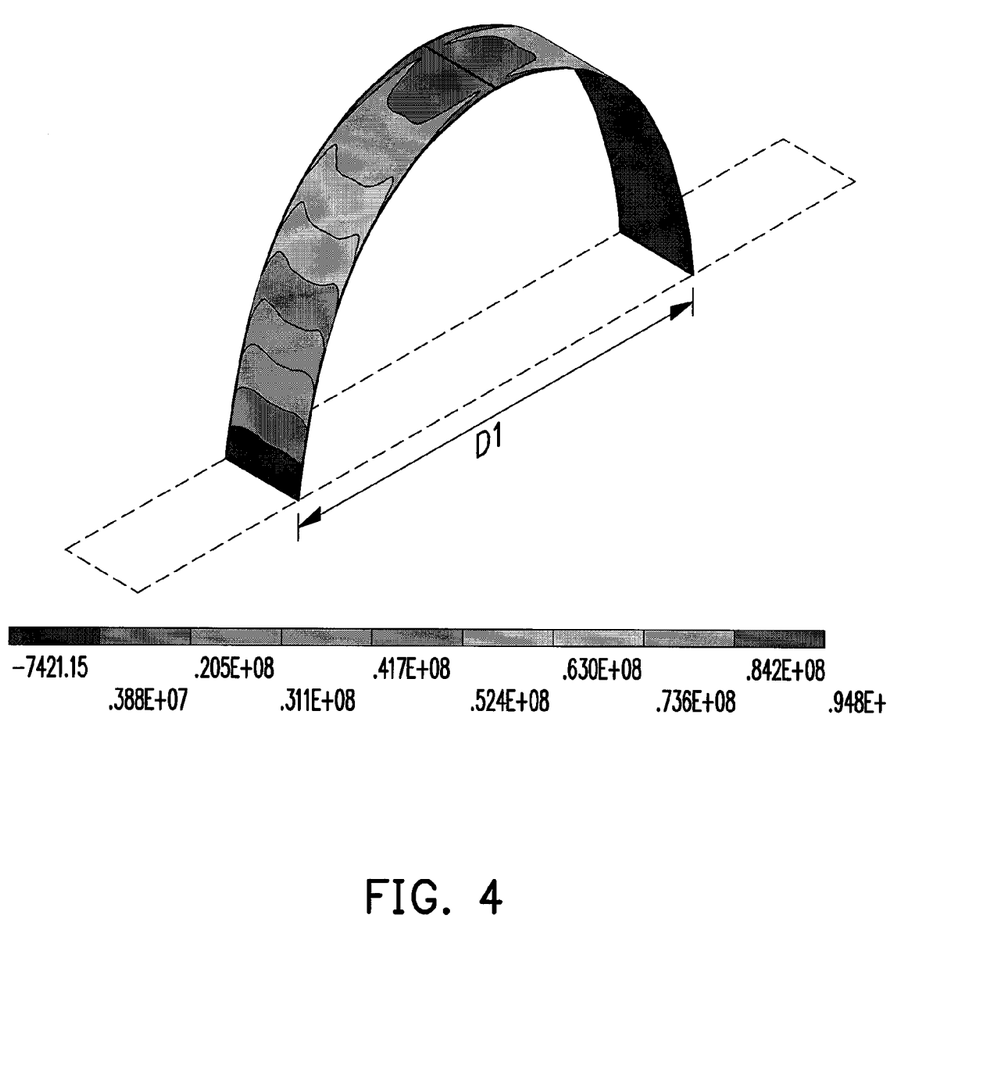
FIG. 4 is a schematic diagram of a stress distribution model of a testing sample according to an embodiment of the disclosure.

FIG. 4 is a schematic diagram of a stress distribution model of the testing sample according to an embodiment of the disclosure. Referring to FIG. 1, FIG. 3 and FIG. 4, in step S130, a maximum principle stress value of the stress distribution model 120 or a breaking point principle stress value of the stress distribution model 120 at the breaking point BP when the testing sample 110 breaks is obtained according to the first distance D1 or the second distance D2 obtained in the step S120. In detail, the first distance D1 between the two ends 112 and 114 when the testing sample 110 breaks is input to the stress distribution model of the testing sample 110, i.e. displacement amounts of the two ends 112 and 114 of the testing sample 110 are input to the stress distribution module 120 to obtain the maximum principle stress value or the breaking point principle stress value at the breaking point BP of the stress distribution model 120 of the structure to be tested shown in FIG. 4 through the FEA. It should be noticed that if the maximum principle stress value is calculated according to the first distance D1, i.e. according to the distance between the two ends 112 and 114 when the testing sample 110 breaks, the operation and calculation thereof is relatively simple. Certainly, a designer can also select to obtain the principle stress value of the testing sample 110 at the breaking point BP. The former result is easily obtained, and the latter result is more accurate, and selection thereof is determined by the designer according to an actual application requirement.

Then, a step S140 is executed, by which the steps 120 to 130 are repeated until repeating times reaches a predetermined sample number, so as to obtain the maximum principle stress values or the breaking point principle stress values of a plurality of testing samples, and then a step S150 is executed to perform statistical analysis on the obtained maximum principle stress values or the breaking point principle stress values. In this way, a bending stress strength of the testing samples can be deduced. For example, if the predetermined sample number is 30, the steps 120 to 130 are executed on the 30 testing samples, the first distances D1, the second distances D2 of the 30 testing samples, and the maximum principle stress values and the breaking point principle stress values obtained according to the first distances D1 and the second distances are listed in detail below, where MS represents the maximum principle stress value of the stress distribution model, BS represents the breaking point principle stress value of the stress distribution model at the breaking point.

TABLE 1

| Sample number | D1 (mm) | D2 (mm) | MS (Mpa) | BS (Mpa) |
|---|---|---|---|---|
| 1 | 110.5 | 88 | 94.8 | 92.6 |
| 2 | 104.5 | 82 | 98.7 | 93.6 |
| 3 | 122.5 | 100 | 86.9 | 56.9 |
| 4 | 102.5 | 97.5 | 100 | 99.8 |
| 5 | 129.0 | 91 | 82.5 | 81.4 |
| 6 | 109.0 | 95 | 95.8 | 95.3 |
| 7 | 104.5 | 82 | 98.7 | 93.6 |
| 8 | 102.0 | 92.5 | 100 | 99.3 |
| 9 | 95.5 | 96 | 105 | 104.1 |
| 10 | 108.5 | 98 | 96.2 | 96 |
| 11 | 105.5 | 75 | 98.1 | 88.6 |
| 12 | 92.5 | 90 | 107 | 104.6 |
| 13 | 98.5 | 93 | 103 | 101.6 |
| 14 | 100.0 | 96 | 102 | 101.2 |
| 15 | 100.0 | 97.5 | 102 | 101.4 |
| 16 | 131.5 | 97 | 80.8 | 80.6 |
| 17 | 105.0 | 80 | 98.4 | 92.2 |
| 18 | 113.5 | 76.5 | 92.9 | 85.1 |
| 29 | 101.0 | 78 | 101 | 93.3 |
| 20 | 118.5 | 84 | 89.6 | 86 |
| 21 | 126.5 | 89 | 84.2 | 82.6 |
| 22 | 105.0 | 68 | 98.4 | 83.6 |
| 23 | 108.5 | 73 | 96.1 | 85.5 |
| 24 | 96.5 | 94 | 104 | 103.1 |
| 25 | 112.5 | 64 | 93.5 | 75.9 |
| 26 | 114.5 | 82 | 92.2 | 87.6 |
| 27 | 125.5 | 100 | 84.9 | 84.9 |
| 28 | 94.0 | 79 | 106 | 97.9 |
| 29 | 110.0 | 90 | 95.2 | 93.5 |
| 30 | 102.5 | 80 | 100 | 93.7 |

Statistical analysis is performed according to the above data, for example, average values and standard deviations of the maximum principle stress values and the breaking point principle stress values of the 30 testing samples are respectively calculated, where an average strength of the 30 test samples for resisting the bending stress can be deduced according to the average values, and a statistical dispersion of the maximum principle stress values and the breaking point principle stress values of the 30 testing samples are deduced according to the standard deviations. The average values and standard deviations of the maximum principle stress values and the breaking point principle stress values obtained by performing statistical analysis on the data of the table 1 are listed in detail in a following table 2.

TABLE 2

|  | Average (Mpa) | Standard deviation |
|---|---|---|
| MS (Mpa) | 96.26 | 6.88 |
| BS (Mpa) | 91.18 | 9.94 |

In this way, according to the aforementioned stress data, it can be deduced whether the structure strength of the structure to be tested is enough to resist the bending stress endured during a manufacturing process or during product application. Namely, the stress data can be used as a criterion for determining whether the structure to be tested is safe or whether the structure to be tested is destructed during the manufacturing process and the product application.

In the present embodiment, the testing sample has a testing length, and a method of determining the testing length includes following steps. First, in a first step, a length evaluation sample of a predetermined length is provided. Then, in a second step, a pre-test is performed on the length evaluation sample under a force condition the same with that of the step S120 of FIG. 1 to bend the length evaluation sample till it breaks, so as to obtain a first distance (for example, the first distance D1 shown in FIG. 3) between the two ends of the length evaluation sample when the length evaluation sample breaks. Now, if a ratio between the first distance and the predetermined length when the length evaluation sample breaks is substantially greater than 0.46, namely, the first distance is substantially greater than 0.46 times of the predetermined length, and now the predetermined length is taken as the testing length. If the ratio between the first distance and the predetermined length when the length evaluation sample breaks is substantially smaller than or equal to 0.46, namely, the first distance is substantially smaller than or equal to 0.46 times of the predetermined length, the first step to the second step are repeated by at least once, and another length evaluation product with a shorter predetermined length is provided in the first step until the ratio between the first distance and the predetermined length when the length evaluation sample breaks is substantially greater than 0.46. In this way, the predetermined length of the present length evaluation sample is taken as the testing length.

For example, a length evaluation sample is provided, and the predetermined length thereof is 210 mm. Then, a pre-test is performed on the length evaluation sample under the force condition the same with that of the step S120 to bend the length evaluation sample till it breaks, so as to obtain a first distance between the two ends of the length evaluation sample when the length evaluation sample breaks. Now, if the first distance is substantially smaller than 0.46 times of the predetermined length (i.e. 96.6 mm) when the length evaluation sample breaks, a length evaluation product with a predetermined length (for example, 200 mm) shorter than the predetermined length (210 mm) of the previous length evaluation sample is provided, and the aforementioned pre-test is performed on such length evaluation sample. Now, if the first distance is substantially greater than 0.46 times of the predetermined length when the length evaluation sample breaks, the predetermined length of 200 mm can be taken as the testing length of the length evaluation sample of the present embodiment. If the first distance is still substantially not greater than 0.46 times of the predetermined length when the length evaluation sample breaks, a length evaluation product shorter than the length evaluation sample with the predetermined length of 200 mm is further provided to take the aforementioned pre-test till when the length evaluation sample breaks, the first distance is substantially greater than 0.46 times of the predetermined length, and the predetermined length of such length evaluation sample is taken as the testing length of the testing sample of the present embodiment.

In another embodiment of the disclosure, the method of determining the testing length may further include following steps. First, the aforementioned first step is executed, i.e. a length evaluation sample of a predetermined length is provided. Then, the aforementioned second step is executed, i.e. a pre-test is performed on the length evaluation sample under a force condition the same with that of the step S120 of FIG. 1 to bend the length evaluation sample till it breaks, so as to obtain a first distance between the two ends of the length evaluation sample when the length evaluation sample breaks. Then, a third step is executed, by which if the ratio between the first distance and the predetermined length when the length evaluation sample breaks is substantially greater than 0.46, the present predetermined length is taken as a verification length, and if the ratio between the first distance and the predetermined length when the length evaluation sample breaks is substantially smaller than or equal to 0.46, the first step to the second step are repeated by at least once, and another length evaluation product with a shorter predetermined length is provided in the first step until the ratio between the first distance and the predetermined length when the length evaluation sample breaks is substantially greater than 0.46, and the predetermined length of the present length evaluation sample is taken as the verification length. Then, the first step to the third step is repeated by at least once to obtain a plurality of different verification lengths, so as to determine the testing length of the testing sample according to the different verification lengths.

In brief, the method for determining the testing length of the present embodiment is similar to the method of the previous embodiment, and a difference there between is that in the present embodiment, the steps of the previous embodiment are repeated by at least once to obtain a plurality of different verification lengths, and then bending strength test data of different length evaluation samples with different verification lengths are compared, and a suitable testing length is determined by comparing the bending strength test data of different length evaluation samples. Theoretically, regarding the different length evaluation samples with different verification lengths obtained by repeating the steps of the previous embodiment, the bending strength test data thereof are substantially the same, but for the sake of prudence in engineering practice, repeated verifications are performed to determine a more accurate and suitable testing length.

In the present embodiment, a size of the testing sample is 200×20×0.1 mm, and the testing sample is, for example, obtained through laser cutting, etc. An ultraviolet (UV) laser used for cutting the testing sample to the aforementioned size has a power of, for example, 3 watts, a light spot of about 30 µm, a frequency of about 40 kHz and a wavelength of about 355 nm. The present embodiment is only used as an example, and the size of the testing sample, the method for cutting the testing sample and the cutting parameters used for cutting the testing sample are not limited by the disclosure.

Figure 5:
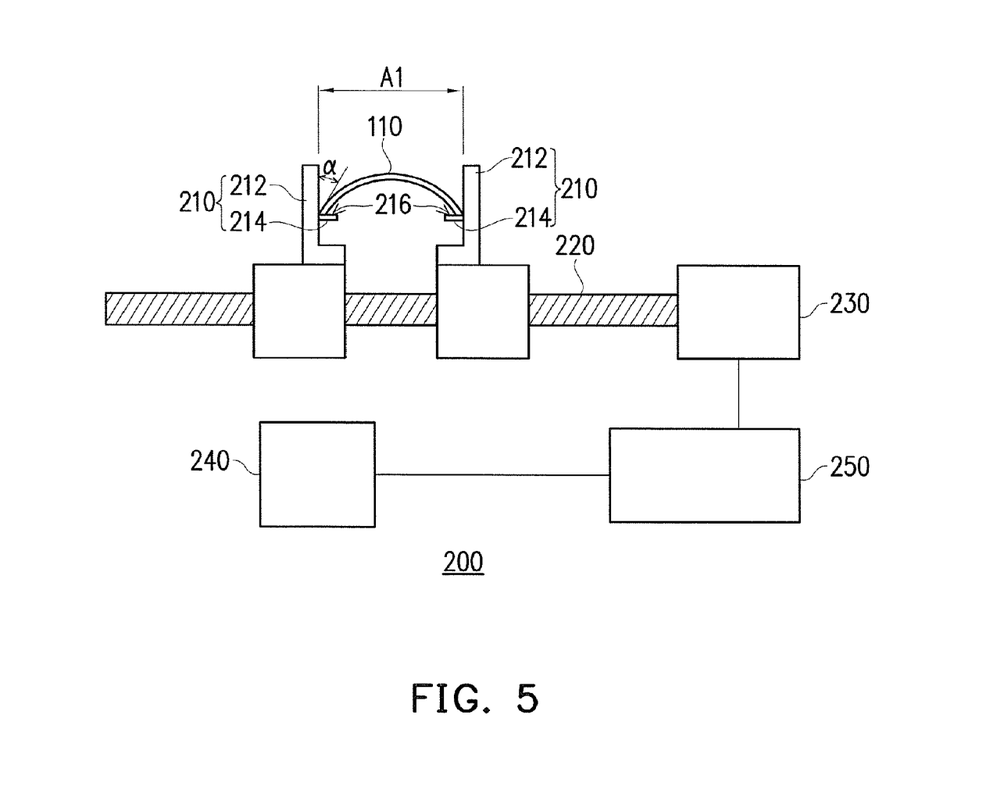
FIG. 5 is a schematic diagram of a testing apparatus of bending stress according to an embodiment of the disclosure.

FIG. 5 is a schematic diagram of the testing apparatus of bending stress according to an embodiment of the disclosure. In the present embodiment, the aforementioned testing method of bending stress can be executed through the testing apparatus 200 of bending stress shown in FIG. 5. Referring to FIG. 5, the testing apparatus 200 of bending stress of the present embodiment includes two fixtures 210 and a transmission unit 220. The two fixtures 210 are disposed opposite to each other, and are adapted to move relative to each other along an axial direction A1. The two fixtures 210 respectively have a carrying portion 216 for leaning against the two ends of the testing sample 110. The transmission unit 220 is coupled to the two fixtures 210 to drive the two fixtures 210 to move relative to each other along the axial direction A1 to bend the testing sample 110. The transmission unit 220 is, for example, a lead screw, a belt pulley, gear and rack or a rope pulley, etc. Therefore, according to the step S120 of the testing method of bending stress, the force is applied on the two ends of the testing sample 110 to bend the testing sample 110. In the present embodiment, each of the fixtures 210 includes a body 212 and a pin 214. The pin 214 is inserted to the surface of the body 212 to form the carrying portion 216 having an L-shaped cross-section, where the two ends of the testing sample 110 respectively lean against corners of the L-shaped cross-sections of the carrying portions 216 of the two fixtures 210. In this way, when the two ends of the testing sample 110 are bended under the force, the fixtures 210 support the testing sample 110 only through the carrying portions 216 with the L-shaped cross-section, so that a problem that the fixtures 210 are difficult to clamp the testing sample 110 when the size thereof is too small or the fixtures 210 are easy to damage the surface of the testing sample 110 can be mitigated. Moreover, by using the pins 214 to support the testing sample 110, a contact area between the testing sample 110 and the fixtures 210 is decreased, and a friction force between the testing sample 110 and the fixtures 210 is accordingly decreased, such that testing accuracy of the bending stress is enhanced.

In the present embodiment, the testing apparatus of bending stress may further include a driving unit 230, a sensing unit 240 and a control unit 250. The driving unit 230 is coupled to the transmission unit 220 to drive the transmission unit 220 to move along the axial direction A1, so as to drive the two fixtures 210 to move relative to each other along the axial direction A1. In the present embodiment, the driving unit 230 is, for example, an electric motor, a pneumatic device or a hydraulic device, etc. The sensing unit 240 is used to sense whether the testing sample 110 is bended to break. In the present embodiment, the sensing unit 240 can be sound sensing unit, a visual sensing unit or an optical sensing unit, etc. Namely, the sensing unit 240 can detect a breaking time point of the testing sample 110 through an acoustic, visual or optical method. The control unit 250 is coupled to the driving unit 230 and the sensing unit 240. When the sensing unit 240 detects that the testing sample 110 breaks, the control unit 250 controls the driving unit 230 to stop activation, so as to stop driving the transmission unit 220 to continually moving along the axial direction A1.

In summary, in the disclosure, by applying a force on the two ends of the testing sample of the structure to be tested till the testing sample breaks at a breaking point, the first distance between the two ends of the testing sample when the testing sample breaks or the second distance from the breaking point to a closer end of the two ends is obtained. The maximum principle stress value of the stress distribution model or the breaking point principle stress value of the stress distribution model at the breaking point is obtained by inputting the first distance and the second distance to the stress distribution model of the structure to be tested, so as to deduce a strength that the structure to be tested resist the bending stress to serve as a criterion for determining whether the structure to be tested is safe or whether the structure to be tested is destructed during the manufacturing process and the product application.

Moreover, in the disclosure, two fixtures capable of moving relative to each other along the axial direction of the testing sample are used to apply a force on the two ends of the testing sample. The two ends of the testing sample respectively lean against the carrying portions with the L-shaped cross-section of the two fixtures without being clamped by the fixtures, such that the problem that the fixtures are difficult to clamp the testing sample when the size thereof is too small or the fixtures are easy to damage the surface of the testing sample can be mitigated. Moreover, the carrying portion with the L-shaped cross-section is formed by inserting the pin to the body of the fixture, such that the testing sample is only supported by the pins, by which the contact area between the testing sample and the fixtures is decreased, and the friction force between the testing sample and the fixtures is accordingly decreased, such that the testing accuracy of the bending stress is enhanced.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A testing method of bending stress, comprising:
   (a) building a stress distribution model;
   (b) providing a testing sample, and applying a force on two ends of the testing sample to bend the testing sample till the testing sample breaks at a breaking point, so as to obtain a first distance between the two ends of the testing sample when the testing sample breaks, and a second distance from the breaking point to a closer end of the two ends; and
   (c) obtaining a maximum principle stress value of the stress distribution model or a breaking point principle stress value of the stress distribution model at the breaking point when the testing sample breaks according to the first distance or the second distance.

2. The testing method of bending stress as claimed in claim 1, further comprising:
   repeating the step (b) to the step (c) till repeating times reaches a predetermined sample number, so as to obtain the maximum principle stress values or the breaking point principle stress values of a plurality of testing samples; and
   performing statistical analysis on the maximum principle stress values or the breaking point principle stress values.

3. The testing method of bending stress as claimed in claim 1, wherein a method of building the stress distribution model comprises finite element analysis (FEA).

4. The testing method of bending stress as claimed in claim 1, wherein the testing sample has a testing length, and a method of determining the testing length comprises:
   (d) providing a length evaluation sample of a predetermined length;
   (e) performing a pre-test on the length evaluation sample under a force condition the same with that of the step (b) to bend the length evaluation sample till the length evaluation sample breaks, so as to obtain the first distance between the two ends of the length evaluation sample when the length evaluation sample breaks; and
   (f) taking the predetermined length as the testing length when a ratio between the first distance and the predetermined length is substantially greater than 0.46, and repeating the step (d) to the step (e) by at least once when the ratio between the first distance and the predetermined length is substantially smaller than or equal to 0.46, and providing another length evaluation product with a shorter predetermined length in the step (d) until when the length evaluation sample breaks, the ratio between the first distance and the predetermined length is substantially greater than 0.46, and taking the predetermined length of the present length evaluation sample as the testing length.

5. The testing method of bending stress as claimed in claim 1, wherein the testing sample has a testing length, and a method of determining the testing length comprises:
   (d) providing a length evaluation sample of a predetermined length;
   (e) performing a pre-test on the length evaluation sample under a force condition the same with that of the step (b) to bend the length evaluation sample till the length evaluation sample breaks, so as to obtain the first distance between the two ends of the length evaluation sample when the length evaluation sample breaks; and (f) taking the predetermined length as a verification length when a ratio between the first distance and the predetermined length is substantially greater than 0.46, and repeating the step (d) to the step (e) by at least once when the ratio between the first distance and the predetermined length is substantially smaller than or equal to 0.46, and providing another length evaluation product with a shorter predetermined length in the step (d) until when the length evaluation sample breaks, the ratio between the first distance and the predetermined length is substantially greater than 0.46, and taking the predetermined length of the present length evaluation sample as the verification length;

(g) repeating the step (d) to the step (f) by at least once to obtain a plurality of different verification lengths; and (h) determining the testing length of the testing sample according to the different verification lengths.

6. The testing method of bending stress as claimed in claim 1, wherein a method of applying a force on the two ends of the testing sample comprises:

respectively applying a horizontal force opposite to each other on the two ends of the testing sample to make the two ends to approach to each other, and controlling a relative moving rate of the two ends of the testing sample to be smaller than 10 mm/min.

7. The testing method of bending stress as claimed in claim 1, wherein a testing apparatus is used to implement the step (b), and the testing apparatus comprises:

two fixtures, disposed opposite to each other, and adapted to move relative to each other along an axial direction, wherein the two fixtures respectively have a carrying portion for leaning against the two ends of the testing sample, so as to apply the force on the two ends of the testing sample.

8. The testing method of bending stress as claimed in claim 7, wherein each of the fixtures comprises:

a body; and a pin, inserting to a surface of the body to form the carrying portion with an L-shaped cross-section, wherein the two ends of the testing sample respectively lean against corners of the L-shaped cross-sections of the carrying portions of the two fixtures.

9. The testing method of bending stress as claimed in claim 7, wherein the testing apparatus further comprises a transmission unit coupled to the two fixtures and driving the two fixtures to move relative to each other along the axial direction to bend the testing sample.

10. The testing method of bending stress as claimed in claim 9, wherein the testing apparatus further comprises a sensing unit and a control unit, the sensing unit is used to detect whether the testing sample is bended to break, and the control unit is coupled to the sensing unit, and when the sensing unit detects that the testing sample breaks, the control unit controls the transmission unit to stop driving the two fixtures.

* * * * *